(12) United States Patent
Akah et al.

(10) Patent No.: US 12,241,029 B2
(45) Date of Patent: *Mar. 4, 2025

(54) PROCESS FOR THE CONVERSION OF PETROLEUM TO LIGHT OLEFINS UTILIZING A PRETREATMENT COMPLEX AND STEAM ENHANCED CATALYTIC CRACKER

(71) Applicant: Saudi Arabian Oil Company, Dhahran (SA)

(72) Inventors: Aaron Chi Akah, Dhahran (SA); Qi Xu, Dhahran (SA); Musaed Salem Al-Ghrami, Dammam (SA); Zhonglin Zhang, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 196 days.

This patent is subject to a terminal disclaimer.

(21) Appl. No.: 17/865,823

(22) Filed: Jul. 15, 2022

(65) Prior Publication Data

US 2024/0018428 A1    Jan. 18, 2024

(51) Int. Cl.
*C10G 69/06*        (2006.01)
*B01D 3/06*         (2006.01)
(Continued)

(52) U.S. Cl.
CPC .............. *C10G 69/06* (2013.01); *B01D 3/06* (2013.01); *B01J 19/245* (2013.01); *C10J 3/82* (2013.01);
(Continued)

(58) Field of Classification Search
CPC .... C10G 67/0454; C10G 55/06; C10G 49/02; C10G 49/22; C10G 9/36; C10G 69/04;
(Continued)

(56) References Cited

U.S. PATENT DOCUMENTS 2,416,023 A    2/1947   Schulze et al.
3,361,535 A    1/1968   Pollitzer et al.
(Continued)

FOREIGN PATENT DOCUMENTS

EP        3578623 A1    12/2019

OTHER PUBLICATIONS

Akah et al., "An Overview of Light Olefins Production via Steam Enhanced Catalytic Cracking", Catalysis Surveys from Asia, vol. 23, pp. 265-276, 2019.
(Continued)

*Primary Examiner* — Prem C Singh
*Assistant Examiner* — Brandi M Doyle
(74) *Attorney, Agent, or Firm* — DINSMORE & SHOHL LLP

(57) ABSTRACT

A process for the conversion of a petroleum feed to light olefins may comprise pretreating the petroleum feed to form one or more pretreated petroleum feeds and fractionating the one or more pretreated petroleum feeds to form a methane stream, an ethane stream, a $C_3$-$C_4$ stream, a light liquid fraction, and a heavy liquid fraction. The process may further comprise methane cracking the methane stream to form hydrogen, steam cracking the ethane stream to form a steam cracking product; dehydrogenating the $C_3$-$C_4$ stream to form a dehydrogenated stream; and steam enhanced catalytic cracking (SECC) the light liquid fraction and the heavy liquid fraction to form an SECC product.

16 Claims, 2 Drawing Sheets

(51) Int. Cl.
  *B01J 19/24* (2006.01)
  *C10J 3/82* (2006.01)
(52) U.S. Cl.
  CPC . *B01J 2219/0004* (2013.01); *C10G 2300/206* (2013.01); *C10G 2300/308* (2013.01); *C10G 2300/4006* (2013.01); *C10G 2300/4012* (2013.01); *C10G 2400/20* (2013.01); *C10G 2400/30* (2013.01); *C10J 2300/1603* (2013.01)
(58) Field of Classification Search
  CPC ...... C10G 69/14; C10G 21/003; C10G 51/04; C10G 51/06; C10G 11/20; C10G 2300/301; C10G 2300/4081; C10G 2300/1033; C10G 2300/4018; C10G 2300/42; C10G 2300/4012; C10G 2300/807; C10G 2300/4006; C10G 2400/20; C10G 2400/30
  See application file for complete search history.

(56) References Cited

U.S. PATENT DOCUMENTS

| | | | |
|---|---|---|---|
| 3,702,292 A | 11/1972 | Burich | |
| 3,775,293 A | 11/1973 | Watkins | |
| 3,784,463 A | 1/1974 | Reynolds et al. | |
| 4,111,793 A | 9/1978 | Kolombos et al. | |
| 6,660,158 B1 | 12/2003 | Ellingsen | |
| 6,740,788 B1 | 5/2004 | Maher et al. | |
| 7,491,315 B2 | 2/2009 | Eng et al. | |
| 8,631,311 B1 | 1/2014 | Chan et al. | |
| 8,685,232 B2 | 4/2014 | Mandal et al. | |
| 9,228,140 B2 | 1/2016 | Abba et al. | |
| 10,138,177 B2 | 11/2018 | Ward et al. | |
| 10,316,258 B2 | 6/2019 | Rispoli et al. | |
| 10,407,630 B2 | 9/2019 | Al-Ghamdi et al. | |
| 10,472,580 B2 | 11/2019 | Al-Ghamdi et al. | |
| 10,717,941 B2 | 7/2020 | Al-Ghamdi et al. | |
| 11,242,493 B1 | 2/2022 | Xu et al. | |
| 2006/0042999 A1 | 3/2006 | Iqbal et al. | |
| 2008/0223754 A1 | 9/2008 | Subramanian et al. | |
| 2009/0143631 A1 | 6/2009 | Gracey et al. | |
| 2009/0294328 A1 | 12/2009 | Iqbal | |
| 2010/0037909 A1 | 2/2010 | Gross et al. | |
| 2010/0317909 A1 | 12/2010 | Keyvanloo et al. | |
| 2013/0112593 A1* | 5/2013 | Montanari | C10G 67/049 208/57 |
| 2013/0248419 A1 | 9/2013 | Abba et al. | |
| 2016/0369189 A1 | 12/2016 | Ward et al. | |
| 2017/0058214 A1* | 3/2017 | Oprins | C10G 9/36 |
| 2018/0142167 A1 | 5/2018 | Al-Ghamdi et al. | |
| 2018/0155633 A1 | 6/2018 | Al-Ghamdi et al. | |
| 2018/0305623 A1 | 10/2018 | Al-Ghrami et al. | |
| 2019/0225894 A1* | 7/2019 | Bourane | B01J 8/003 |
| 2020/0115645 A1 | 4/2020 | Al-Ghamdi et al. | |
| 2020/0392055 A1 | 12/2020 | Nesterenko et al. | |
| 2021/0087476 A1 | 3/2021 | Boualleg et al. | |
| 2021/0139793 A1 | 5/2021 | Al-Shafei et al. | |
| 2021/0246388 A1 | 8/2021 | Koseoglu | |
| 2022/0017829 A1 | 1/2022 | Al-Shafei et al. | |
| 2022/0064548 A1 | 3/2022 | Akah et al. | |
| 2022/0064556 A1 | 3/2022 | Akah et al. | |

OTHER PUBLICATIONS

US Office Action dated Apr. 14, 2023 pertaining to U.S. Appl. No. 17/865,787, filed Jul. 15, 2022, pp. 1-24.
Notification of Transmittal of the International Search Report and the Written Opinion of the International Searching Authority, or the Declaration dated Oct. 12, 2023 pertaining to International application No. PCT/US2023/070020 filed Jul. 12, 2023, pp. 1-11.
U.S. Office Action dated Mar. 24, 2023 pertaining to U.S. Appl. No. 17/865,995, filed Jul. 15, 2022, pp. 1-21.
U.S. Office Action dated Mar. 27, 2023 pertaining to U.S. Appl. No. 17/866,029, filed Jul. 15, 2022, pp. 1-22.
U.S. Office Action dated Mar. 27, 2023 pertaining to U.S. Appl. No. 17/866,035, filed Jul. 15, 2022, pp. 1-21.

* cited by examiner

PROCESS FOR THE CONVERSION OF PETROLEUM TO LIGHT OLEFINS UTILIZING A PRETREATMENT COMPLEX AND STEAM ENHANCED CATALYTIC CRACKER

FIELD

Embodiments of the present disclosure generally relate to the conversion of petroleum to basic intermediates, and more specifically, to the conversion of crude oil to light olefins.

INTRODUCTION

Light olefins (such as ethylene, propylene, and butylene) and aromatics (such as benzene, toluene, and xylene) are basic chemical intermediates used widely in the petrochemical and chemical industries. Thermal cracking and steam pyrolysis are the major types of processes for forming these materials. Typical feedstocks for steam pyrolysis include petroleum gases, such as ethane, and distillates such as naphtha, kerosene, and gas oil. The availability of these feedstocks is limited and requires costly and energy-intensive process steps before conversion to the basic intermediates.

Many chemical producers are further limited by the supply and quality of feed from nearby refiners, due to reliance on oil refinery by-products as feed. Chemical producers are also limited by the high cost of oil refining and its associated fuel markets. These may negatively influence the economic value of refinery sourced feeds. Higher global fuel efficiency standards for vehicles will further reduce fuel demand and narrow refinery margins. This may complicate the economics of the chemical supply markets.

Accordingly, there remains a need for improved processes and systems for directly converting crude oil to basic chemical intermediates, such as lower olefins and aromatics.

SUMMARY

Embodiments of the present disclosure address this need for increased yields of light olefins from crude oils by providing processes and systems specifically tailored to convert most parts of a crude oil to light olefins and recycling or upgrading the rest, thereby maximizing the financial value of the crude oil.

In accordance with one embodiment of the present disclosure, a process for the conversion of a petroleum feed to light olefins may comprise pretreating the petroleum feed to form one or more pretreated petroleum feeds and fractionating the one or more pretreated petroleum feeds to form a methane stream, an ethane stream, a $C_3$-$C_4$ stream, a light liquid fraction, and a heavy liquid fraction. The process may further comprise methane cracking the methane stream to form hydrogen, steam cracking the ethane stream to form a steam cracking product; dehydrogenating the $C_3$-$C_4$ stream to form a dehydrogenated stream; and steam enhanced catalytic cracking (SECC) the light liquid fraction and the heavy liquid fraction to form an SECC product.

In accordance with another embodiment of the present disclosure, a system for the conversion of a petroleum feed to light olefins may comprise a pretreating complex configured to pretreat a petroleum feed to form one or more pretreated petroleum feeds; a separator 160 fluidly connected to the pretreating complex and configured to fractionate the one or more pretreated petroleum feeds to form a methane stream, an ethane stream, a $C_3$-$C_4$ stream, a light liquid fraction and a heavy liquid fraction; a methane cracker fluidly connected to the separator and configured to methane crack the methane stream to form hydrogen; a steam cracker fluidly connected to the separator and configured to steam crack the ethane stream to form a steam cracking product; a dehydrogenation unit fluidly connected to the separator and configured to dehydrogenate the $C_3$-$C_4$ stream to form a dehydrogenated stream; and one or more steam enhanced catalytic crackers fluidly connected to the separator and configured to steam enhanced catalytic crack the light liquid fraction and the heavy liquid fraction to form a steam enhanced catalytically cracked product.

Although the concepts of the present disclosure are described herein with primary reference to crude oil and light olefins, it is contemplated that the concepts will enjoy applicability to any petrochemical feed and any basic chemical intermediates.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

"API" means American Petroleum Institute.
"$C_x$" means a molecule with x number of carbons.
"° C." means degrees Celsius.
"mol. %" means mol percent.
"MPa" means megapascals.
"SECC" means steam enhanced catalytic cracking.
"wt." means weight.
"wt. %" or "wt. %" means weight percent.

Figure 1:
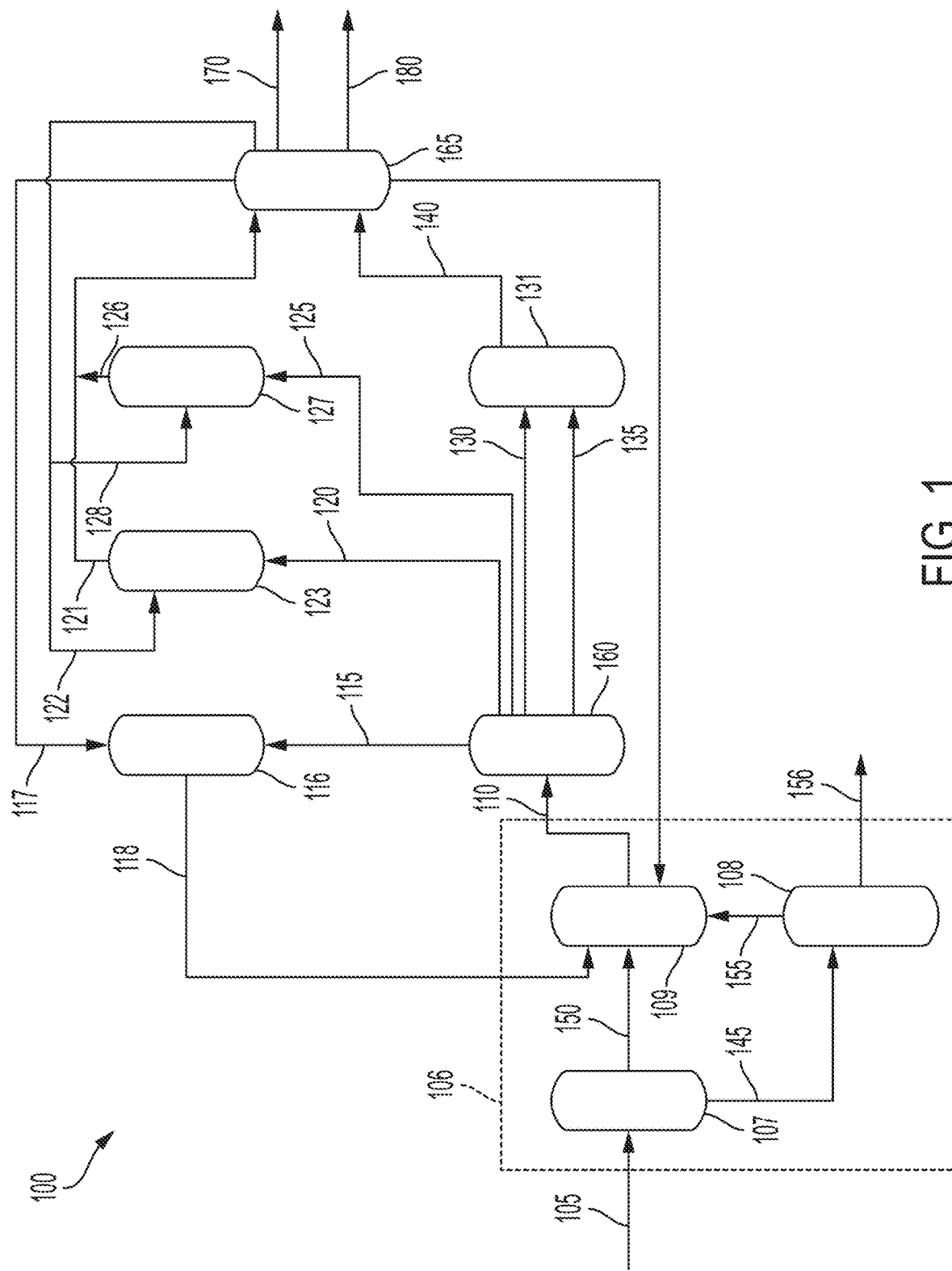
FIG. 1 is a schematic view of embodiments of the present disclosure.

As illustrated in FIG. 1, and as discussed in further detail herein, a system 100 for the conversion of a petroleum feed 105 to light olefins may comprise a pretreating complex 106 configured to pretreat a petroleum feed 105 to form one or more pretreated petroleum feeds 110; a separator 160 fluidly connected to the pretreating complex 106 and configured to fractionate the one or more pretreated petroleum feeds 110 to form a methane stream 115, an ethane stream 120, a $C_3$-$C_4$ stream 125, a light liquid fraction 130 and a heavy liquid fraction 135; a methane cracker 116 fluidly connected to the separator 110 and configured to methane crack the methane stream 115 to form hydrogen 118; a steam cracker 123 fluidly connected to the separator 110 and configured to steam crack the ethane stream 120 to form a steam cracking product 121; a dehydrogenation unit 127 fluidly connected to the separator 110 and configured to dehydrogenate the $C_3$-$C_4$ stream 125 to form a dehydrogenated stream 126; and one or more steam enhanced catalytic crackers 131 fluidly connected to the separator 110 and configured to steam enhanced catalytic crack the light liquid fraction 130 and the heavy liquid fraction 135 to form a steam enhanced catalytically cracked product 140.

While FIG. 1 appears to show only one steam enhanced catalytic cracker 131, it should be understood that 131 may illustrate one or more (i.e. multiple) steam enhanced catalytic crackers, particularly a first steam enhanced catalytic cracker and a second steam enhanced catalytic cracker, together encompassing the steam enhanced catalytic crackers 131. The illustration of one steam enhanced catalytic cracker for 131 is meant for simplification of the flow patterns of FIG. 1.

Further, it should be understood that the use of "light" and "heavy" as identifiers for the one or more steam enhanced catalytic crackers 131 are used simply for the purpose of referencing the feed streams that may enter the one or more steam enhanced catalytic crackers 131. For example, the light (also referred to herein as the "first") steam enhanced catalytic cracker may be understood to have lighter hydrocarbon feeds that have lower boiling points than the feeds for heavy steam enhanced catalytic cracker. Similarly, the heavy (also referred to herein as the "second") steam enhanced catalytic cracker may be understood to have heavier hydrocarbon feeds that have higher boiling points than the feeds for the light steam enhanced catalytic cracker.

The system 100 may further comprise a product separator 165 fluidly connected to the methane cracker, the steam cracker, the dehydrogenation unit, the one or more steam enhanced catalytic crackers, and the pretreating complex. The pretreating complex 106 may further comprise a solvent deasphalting unit 107, a gasification unit 108, and a hydroprocessing unit 109. The hydroprocessing unit 109 may comprise a hydrocracker, a hydrotreater, or both. The pretreating complex may be fluidly connected to the gasification unit 108 and the hydroprocessing unit 109 and may produce a deasphalted oil stream 150 and an asphaltene stream 145 from the petroleum feed 105. The gasification unit may be fluidly connected to the hydroprocessing unit 109 and may produce a hydrogen rich stream 155 and a carbon rich stream 156 from the asphaltene stream 145. The hydroprocessing unit may be fluidly connected to the separator 160 and may be configured to produce the one or more pretreated petroleum feeds 110 from the deasphalted oil stream 150. The hydroprocessing unit may be additionally configured to use at least one of the hydrogen rich stream 155 and the hydrogen 118 to produce the one or more pretreated petroleum feeds 110.

Figure 2:
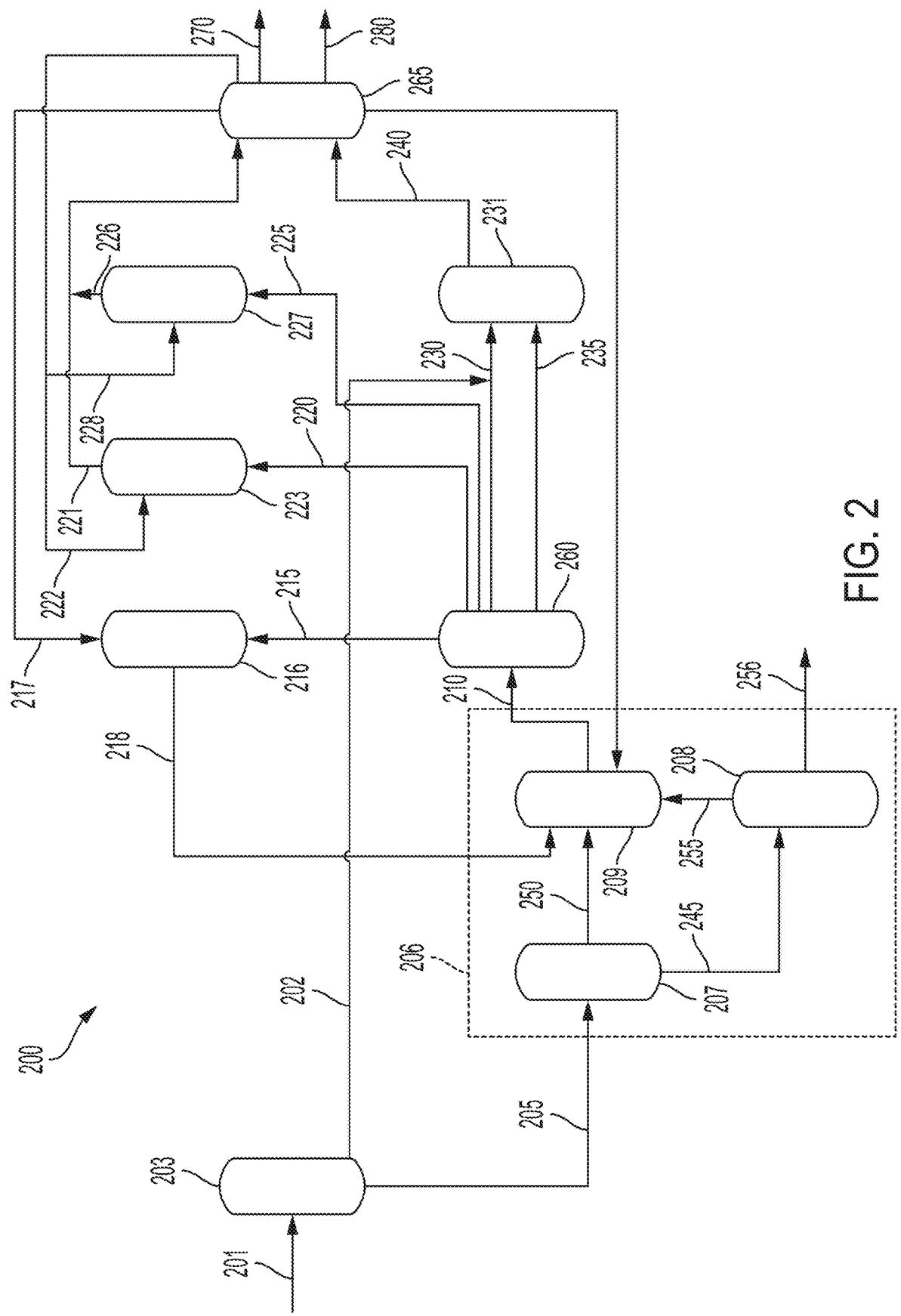
FIG. 2 is a schematic view of embodiments of the present disclosure.

As illustrated in FIG. 2, and as discussed in further detail herein, a system 200 for the conversion of a petroleum feedstock to light olefins may include any of the components of system 100. The system 200 may also further comprise a flash tank 203. The flash tank may be fluidly connected to the pretreating complex and the one or more steam enhanced catalytic crackers. The flash tank 203 may be configured to fractionate a whole crude 201 into a light crude fraction and the petroleum feed. The flash tank may send the light crude fraction to the one or more steam enhanced catalytic crackers.

Also as illustrated in FIG. 1, a process for the conversion of a petroleum feed 105 to light olefins may utilize any of the systems previously discussed and may also comprise pretreating the petroleum feed 105 to form one or more pretreated petroleum feeds 110. The process may then comprise fractionating the one or more pretreated petroleum feeds 110 to form a methane stream 115, an ethane stream 120, a $C_3$-$C_4$ stream 125, a light liquid fraction 130, and a heavy liquid fraction 135. The process may further comprise methane cracking the methane stream 115 to form hydrogen, steam cracking the ethane stream 120 to form a steam cracking product 126, dehydrogenating the $C_3$-$C_4$ stream 125 to form a dehydrogenated stream 126, and steam enhanced catalytic cracking (SECC) the light liquid fraction 130 and the heavy liquid fraction 135 to form an SECC product 140.

As illustrated in FIG. 1, the petroleum feed 105 may be a whole crude. As illustrated in FIG. 2, the petroleum feed 205 may be a portion of a whole crude. A whole crude 201 may be fractionated into a light crude fraction 202 and a petroleum feed 205. The whole crude 201 may be fractionated into the light crude fraction 202 and the petroleum feed 205 in a flash tank 203. The light crude fraction 202 may be subjected to steam enhanced catalytic cracking (SECC). The light crude fraction 202 may be subjected to SECC alone. Alternatively, the light crude fraction 202 may be combined with one or both of the light liquid fraction 230 and the heavy liquid fraction 240 and the combined stream may be subjected to SECC. In some embodiments, the light crude fraction 202 may not be subjected to any further processing before SECC, besides optionally combining the light crude fraction 202 with other streams before SECC the combined stream. The light crude fraction 202 may comprise hydrocarbons with a boiling point of less than 300° C. For example, at least 50 wt. %, at least 60 wt. %, at least 70 w. %, at least 80 wt. %, at least 90 wt. %, at least 95 wt. % of the light crude fraction may have a boiling point less than 300° C.

The whole crude 105, 201 may have an API gravity of from 10° to 40° and a sulfur content of from 0.05 wt. % to 5.00 wt. % sulfur. The whole crude may be an Arab Extra Light, an Arab Light, or an Arab Heavy crude. Arab Extra Light crude may be a crude oil originating in Saudi Arabia. Arab Extra Light crude may have an API gravity of from 33° to 40° and a sulfur content of from 0.05 to 1.5 wt. %. For Example, Arab Extra Light crude may have an API gravity of about 40.0° and a sulfur content of about 1.09 wt. %. Arab Light crude may be a crude oil originating in Saudi Arabia. Arab Light crude may have an API gravity of from 30° to 33° and a sulfur content of from 1.2 to 2.0 wt. %. For Example, Arab Extra Light crude may have an API gravity of about 32.8° and a sulfur content of about 1.97 wt. %. Arab Heavy crude may be a crude oil originating in Saudi Arabia. Arab Heavy crude may have an API gravity of from 10° to 30° and a sulfur content of from 2.0 to 5.0 wt. %. For Example, Arab Light crude may have an API gravity of about 27.7° and a sulfur content of about 2.87 wt. %.

Referring again to FIG. 1, the petroleum feed 105 may be pretreated in a pretreating complex 106. The pretreating complex 106 may comprise a solvent deasphalting unit 107, a gasifier 108, and a hydroprocessing unit 109, such as a hydrotreater or hydrocracker. Pretreating the petroleum feed 105 may comprise solvent deasphalting the petroleum feed 105. Solvent deasphalting the petroleum feed 105 may produce one or both of an asphaltene stream 145 and a deasphalted oil stream 150. Solvent deasphalting the petroleum feed 105 may comprise contacting the petroleum feed 105 with a solvent at a deasphalting temperature, a deasphalting pressure, and a deasphalting solvent/feed ratio. The solvent may comprise a light paraffinic solvent, such $C_3$ to $C_7$ paraffins, such as propane. The solvent may also be a light paraffinic hydrocarbon, such as, but not limited to n-propane, n-butane, n-pentane, n-hexane, n-heptane, or combinations thereof. The deasphalting temperature may be from 120 to 160° C. The deasphalting pressure may be from 2 to 6 MPa, from 3 to 5 MPa, or from 3.5 to 4.5 MPa. The solvent/feed ratio may be from 3 to 6, from 4 to 5, or from 4.25 to 4.76.

The deasphalted oil stream 150 may comprise less than 10.0 wt. % asphaltenes. The deasphalted oil stream 150 may comprise from 15 to 60 wt. % aromatics, from 30 to 80 wt. % saturates, and from 0.2 to 4.5 wt. % sulfur. The deasphalted oil stream 150 may have a viscosity of from 5 to 60 centipoise at a shear rate of 0.1 to 10 s$^{-1}$ and a temperature of 25° C. The asphaltene stream 145 may comprise from 25 to 100 wt. % asphaltenes. The asphaltene stream may have a viscosity of from 20 to 480 centipoise at a shear rate of 0.1-10 s$^{-1}$ and a temperature of 60° C. In embodiments, the asphaltene stream 145 may further include non-hydrocarbon constituents and impurities. In this way, the solvent deasphalting unit 107 may remove asphaltenes, non-hydrocarbon constituents, impurities, or combinations thereof, from the petroleum feed 105 to form the deasphalted oil stream 150. For example, the solvent deasphalting unit 107 may remove nitrogen-containing compounds, sulfur-containing compounds, Conradson carbon residue (CCR), and metal compounds such as nickel and vanadium. In embodiments, removing non-hydrocarbon constituents and impurities like the immediately previous may increase the efficiency of downstream treatment units by reducing the coking deactivation rate of the various catalysts used therein.

Pretreating the petroleum feed 105 may comprise gasification of an asphaltene stream 145. Gasification of the asphaltene stream 145 may comprise exposing the asphaltene stream 145 to a low oxygen environment, such as less than 10 mol. %, less than 5 mol. %, less than 2.5 mol. %, less than 1 mol. %, less than 0.5 mol. %, or even less than 0.1 mol. % $O_2$. Gasification may comprise exposing the asphaltene stream 145 to a temperature of from 700° C. to 1200° C. and a pressure of 1 to 29 bar, while in the low oxygen environment. Gasification of the asphaltene stream 145 may produce hydrogen, carbon monoxide, or both. The hydrogen may also be contained in a hydrogen rich stream 155. The hydrogen rich stream 155 may be at least 50 wt. %, at least 60 wt. %, at least 70 wt. %, at least 80 wt. %, at least 90 wt. %, at least 95 wt. %, at least 99 wt. %, or at least 99.9 wt. % hydrogen gas. The carbon monoxide may be combined with the hydrogen rich stream 155 or it may be separated and removed in a carbon rich stream 156. Carbon rich stream 156 may be at least 50 wt. %, at least 60 wt. %, at least 70 wt. %, at least 80 wt. %, at least 90 wt. %, at least 95 wt. %, at least 99 wt. %, or at least 99.9 wt. % carbon monoxide. In embodiments, gasification of the asphaltenes stream 145 may produce hydrogen to carbon monoxide in a weight percent ratio of from 1:5 to 1:2 hydrogen to carbon monoxide. This may also include any weight percent ratio in between 1:5 to 1:2, such as, for example, 1:4, 1:3, 1:4.5, 1:3.5, or 1:2.5, as well as any combination of ratios therein.

Pretreating the petroleum feed 105 may comprise hydroprocessing the deasphalted oil stream 150. Hydroprocessing the deasphalted oil stream 150 may comprise hydrocracking or hydrotreating the deasphalted oil stream 150. Hydroprocessing the deasphalted oil stream 150 may comprise contacting the deasphalted oil stream 150 with hydrogen at a temperature of from 280° C. to 450° C. and a pressure of from 5 bar to 160 bar. The hydrogen may be derived from the hydrogen rich stream 155 produced by the gasification process. In some embodiments, at least some of the hydrogen may be produced by other means, such as electrochemically, by a water-gas shift reaction, or by a methane cracker.

As previously discussed, hydroprocessing the deasphalted oil stream may be classified as hydrocracking. Hydrocracking the deasphalted oil stream may comprise contacting the deasphalted oil stream with hydrogen gas in the presence of a catalyst. The catalyst may be a bifunctional catalyst with an acid function and a hydrogenation function. The catalyst may comprise halogenated alumina, zeolites, amorphous silica-alumina, or clay. As previously discussed, hydroprocessing the deasphalted oil stream may also be classified as hydrotreating. Hydrotreating the deasphalted oil stream may comprise contacting the deasphalted oil stream with a desulfurization catalyst and a denitrogenation catalyst, in the presence of hydrogen. These catalysts may be in sequential beds or may be combined in a single bed. The desulfurization catalyst may comprise cobalt and molybdenum. The denitrogenation catalyst may comprise alumina, nickel-molybdenum, or both.

Referring again to FIG. 1, the pretreated petroleum feed 110 may be fractionated in a separator 160 to form a methane stream 115, an ethane stream 120, a $C_3$-$C_4$ stream 125, a light liquid fraction 130, and a heavy liquid fraction 135. Fractionating of the petroleum feed may occur in a single separator 160 (as illustrated), such as a distillation column, or in several separators operating in series.

The methane stream 115 may be at least 50 wt. %, at least 60 wt. %, at least 70 wt. %, at least 80 wt. %, at least 90 wt. %, at least 95, wt. %, at least 99 wt. %, or even at least 99.9 wt. % methane gas. The methane stream 115 may be substantially free of impurities, such as Sulphur. The methane stream 115 may be subjected to methane cracking. Methane cracking may comprise exposing the methane stream 115 to a methane cracking catalyst in a methane cracker 116. The methane cracking catalyst may comprise one or more of Ni/$CeO_2$, Ni$La_2O_3$, Ni/$SiO_2$, Ni/Mg—O—Al, Fe/$CeO_2$, Fe/$La_2O_3$, Fe/$SiO_2$, Ni/$SiO_2$, Fe/$SiO_2$, Co/$SiO_2$, Rh/$Al_2O_3$, Rh/$Al_2O_3$, or $Nd_2O_3$. The methane stream 115 may be exposed to the methane cracking catalyst at a temperature of at least 500° C., at least 600° C., at least 650° C., at least 700° C., at least 750° C., from 500 to 1000° C., from 600 to 1000° C., from 700 to 1000° C., from 600 to 900° C., from 650 to 850° C., or any subset thereof.

Methane cracking the methane stream 115 may produce hydrogen. The hydrogen may be contained within a methane cracked hydrogen stream 118. The methane cracked hydrogen stream 118 may be at least 50 wt. %, at least 60 wt. %, at least 70 wt. %, at least 80 wt. %, at least 90 wt. %, at least 95, wt. %, at least 99 wt. %, or even at least 99.9 wt. % hydrogen gas. The hydrogen gas may be sent to the hydrotreater or may be used in outside processes. The methane cracker 116 may further produce a solid carbon material. The process may further comprise methane cracking a methane recycle stream 117. For example, the methane recycle stream 117 may comprise at least 50 wt. %, at least 60 wt. %, at least 70 wt. %, at least 80 wt. %, at least 90 wt. %, or at least 95 wt. % methane. The methane recycle stream 117 may be separated from the other components in the product separator 165.

The ethane stream 120 may comprise at least 50 wt. %, at least 60 wt. %, at least 70 wt. %, at least 80 wt. %, at least 90 wt. %, at least 95, wt. %, at least 99 wt. %, or even at least 99.9 wt. % ethane gas. The ethane stream 120 may be steam cracked in a steam cracker 123 to form a steam cracking product 121. Steam cracking the ethane stream 120 may comprise contacting the ethane stream 120 with steam at a steam cracking temperature, steam cracking pressure, and steam-to-feed ratio. The steam cracking temperature may be from 800 to 950° C., from 800 to 900° C., from 825 to 875° C., or any subset thereof. The steam cracking pressure may be from 0.8 to 5 bar, from to 3 bar, from 0.8 to 1.5 bar, from 0.8 to 1.2 bar, or any subset thereof. The steam-to-feed ratio may be from 0.3 to 0.8. The ethane stream 120 may contact the steam in the absence of a catalyst.

The process may further comprise steam cracking a steam cracking recycle stream 122 in the steam cracker 123. The steam cracking recycle stream 122 may comprise ethane gas. For example, the steam cracking recycle stream may comprise at least 50 wt. %, at least 60 wt. %, at least 70 wt. %, at least 80 wt. %, at least 90 wt. %, or at least 95 wt. % ethane. The ethane gas may be separated from the other components in the product separator 165. The steam cracking product 121 may comprise alkenes, such as ethylene and propylene. For example, the steam cracking product may comprise at least 40 wt. %, at least 50 wt. %, at least 60 wt. %, at least 70 wt. %, at least 80 wt. %, at least 90 wt. %, or at least 95 wt. % of the alkenes.

The $C_3$-$C_4$ stream 125 may comprise at least 50 wt. %, at least 60 wt. %, at least 70 wt. %, at least 80 wt. %, at least 90 wt. %, at least 95, wt. %, at least 99 wt. %, or even at least 99.9 wt. % of a combined weight of $C_3$ and $C_4$ gas. The $C_3$-$C_4$ gas may be alkanes, such as propane and butane. The $C_3$-$C_4$ stream 125 may be dehydrogenated in a dehydrogenator 127 to form a dehydrogenated stream 126. Dehydrogenating the $C_3$-$C_4$ stream 125 may comprise contacting the $C_3$-$C_4$ stream 125 with a dehydrogenation catalyst at a temperature of from 575° C. to 620° C. and a pressure of from 1 to 5 bar, or from 2 to 5 bar. The dehydrogenation catalyst may comprise $CrO_3/Al_2O_3$, Pt—$Sn/Al_2O_3$, or both. The dehydrogenation catalyst may also include a zincosilicate support material, one or more alkali or alkaline earth metals, and one or more platinum group metals. The zincosilicate support material may further include a MFI framework type structure incorporating at least silicon and zinc. As used herein, a "MFI framework type structure" may sometimes be referred to as a ZSM-5 framework type structure. Zeolitic framework types, such as the MFI framework type, are disclosed in "Atlas of Zeolite Framework Types, Fifth Edition" by Baerlcher, Meier, and Olson, the contents of which are incorporated by reference in their entirety.

The process may comprise dehydrogenating a dehydrogenation recycle stream 128. The dehydrogenation recycle stream may comprise $C_3$-$C_4$ alkanes. For example, the dehydrogenation recycle stream may comprise at least 50 wt. %, at least 60 wt. %, at least 70 wt. %, at least 80 wt. %, at least 90 wt. %, or at least 95 wt. % $C_3$-$C_4$ alkanes. The dehydrogenated stream 126 may comprise alkenes, such as propylene and butene. For example, the dehydrogenated stream 126 may comprise at least 50 wt. %, at least 60 wt. %, at least 70 wt. %, at least 80 wt. %, at least 90 wt. %, or at least 95 wt. % alkenes, such as propylene and butene.

The light liquid fraction 130 may comprise from $C_5$ hydrocarbons to a hydrocarbons with a boiling point of 300° C. at 1 atmosphere (atm). The heavy liquid fraction 135 may comprise hydrocarbons with at least a 300° C. boiling point at 1 atm. The light liquid fraction 130 and the heavy liquid fraction 135 may be subjected to SECC in a steam enhanced catalytic cracker 131. SECC of the two fractions may occur in separate reactors or in the same reactor. SECC of the two fractions may form an SECC product 140. SECC may also comprise exposing the light liquid fraction 130 or the heavy liquid fraction 135, or both to an SECC catalyst at a SECC temperature and a SECC steam/feed weight ratio. The SECC catalyst may comprise ZSM-5. For example, the SECC catalyst may comprise metals supported on ZSM-5. The metal supported on ZSM-5 may comprise one or more of rare earth metals, transition metals, or alkaline earth metals. The metal supported on ZSM-5 may also comprise one or more of La, Ce, Fe, Ca, Mg, or phosphorus.

As previously discussed, SECC of the two fractions may occur in separate reactors. In these embodiments, the steam enhanced catalytic cracker 131 may include a first steam enhanced catalytic cracker and a second steam enhanced cracker. Each steam enhanced catalytic cracker may be fluidly connected to the hydroprocessing unit and may crack a different liquid fraction. For example, and in embodiments, the first steam enhanced catalytic cracker may SECC the light liquid fraction 130, and the second steam enhanced catalytic cracker may SECC the heavy liquid fraction. Each of these crackers may in turn form the SECC product 140, which may in turn include a light SECC liquid product (from the first steam enhanced catalytic cracker) and a heavy SECC liquid product (from the second steam enhanced catalytic cracker). The first and second steam enhanced catalytic crackers may also be in parallel to each other.

In embodiments, the light liquid fraction 130 and the heavy liquid fraction 135 may need to be processed at different conditions in the steam enhanced catalytic cracker 131 to maximize the yield of desired products. In one non-limiting example, the light liquid fraction 130 may require a longer residence time than the heavy liquid fraction 135 to fully treat and convert the light components of the light liquid fraction 130. Additionally, the heavy liquid fraction 135 may require a shorter residence time to avoid excessive coking of the components of the heavy liquid fraction 135.

The first and second steam enhanced catalytic crackers may also generate different distributions of hydrocarbon products with their product streams. For example, the first steam enhanced catalytic cracker may generate a greater proportion of olefins than naphtha range products (including naphtha and gasoline). In embodiments, the first steam enhanced catalytic cracker may generate an olefin to naphtha product ratio of approximately 3.3:1 olefins to naphtha. The first steam enhanced catalytic cracker may also generate an olefin to naphtha product ratio of from 2:1, from 3:1, from 4:1, from 5:1, from 6:1, or from 7:1 olefins to naphtha.

Similarly, the second steam enhanced catalytic cracker may generate a greater proportion of naphtha and gasoline range products rather than olefins. In embodiments, the second steam enhanced catalytic cracker may generate an olefin to naphtha product ratio of 2.5:1 olefin to naphtha. The second steam enhanced catalytic cracker may also generate an olefin to naphtha product ratio of from 2:5:1, from 2:1, from 1.5:1, from 1:1, or from 0.8:1 olefins to naphtha.

In embodiments, the steam in the steam enhanced catalytic cracker may reduce the hydrocarbon partial pressure, which may have the dual effects of increasing yields of light olefins and/or BTX hydrocarbons as well as reducing coke formation. Light olefins like propylene and butylene are mainly generated from catalytic cracking reactions following the carbonium ion mechanism, and as these are intermediate products, they can undergo secondary reactions such as hydrogen transfer and aromatization (leading to coke formation). The steam may increase the yield of light olefins by suppressing these secondary bi-molecular reactions, and reduce the concentration of reactants and products, which favor selectivity towards light olefins. The steam may also suppress secondary reactions that are responsible for coke formation on catalyst surface, which is good for catalysts to maintain high average activation. These factors may show that a large steam-to-oil weight ratio may be beneficial to the production of light olefins.

In embodiments, increasing the steam-to-feed ratio may improve the light olefin yield of the steam enhanced catalytic cracker. A ratio of the flowrate (gas hourly space velocity) of steam to the flowrate (gas hourly space velocity) of the feed (light liquid fraction or heavy liquid fraction) to the steam enhanced catalytic crackers may be from 0.1 to 1.1 times, from 0.1 to 0.8 times, from 0.1 to 0.5 times, from 0.1 to 0.2 times, from 0.2 to 1.1 times, from 0.2 to 0.8 times, from 0.2 to 0.5 times, from 0.3 to 1.1 times, from 0.3 to 0.8 times, from 0.3 to 0.5 times, from 0.5 to 1.1 times, from 0.5 to 0.8 times, or from 0.8 to 1.1 times steam to feed to improve the steam enhanced catalytic cracking process. The SECC steam/feed weight ratio may also be at least 0.3. For example, the SECC steam/feed ratio may also be from 0.3 to 1.0 wt. % steam to feed. Alternatively, the SECC steam/feed weight ratio may be at least 0.2. For example, the SECC steam/feed ratio may be from 0.2 to 2.0 wt. % steam to feed. The SECC product 140 may comprise light olefins, such as ethylene and propylene. For example, the SECC product 140 may comprise at least 20 wt. % light olefins, or from 15 wt. % to 60 wt. % light olefins.

In embodiments, the ratio of steam to feed may be different for the first steam enhanced catalytic cracker and the second steam enhanced catalytic cracker. For example, the second steam enhanced catalytic cracker may have a steam to feed ratio of from 0.8 to 1.0 steam to feed, whereas the first steam enhanced catalytic cracker may have a steam to feed ratio of from 0.2 to 0.8. In embodiments, the higher steam to feed ratio may be beneficial for the heavy fractions due to the need to reduce the viscosity of heavier crude oil fraction as well as atomize the heavy fractions.

In embodiments, the steam may be injected into the first and second steam enhanced catalytic crackers at a gas hourly space velocity of greater than or equal to 0.1 $h^{-1}$, greater than or equal to 0.5 $h^{-1}$, greater than or equal to 1 $h^{-1}$, greater than or equal to 5 $h^{-1}$, greater than or equal to 6 $h^{-1}$, greater than or equal to 10 $h^{-1}$, or even greater than or equal to 15 $h^{-1}$. The steam may be introduced to the steam enhanced catalytic crackers at a gas hourly space velocity of less than or equal to 100 $h^{-1}$, less than or equal to 75 $h^{-1}$, less than or equal to 50 $h^{-1}$, less than or equal to 30 $h^{-1}$, or less than or equal to 20 $h^{-1}$. The steam may be introduced to the steam enhanced catalytic crackers at a gas hourly space velocity of from 0.1 $h^{-1}$ to 100 $h^{-1}$, from 0.1 $h^{-1}$ to 75 $h^{-1}$, from 0.1 $h^{-1}$ to 50 $h^{-1}$, from 0.1 $h^{-1}$ to 30 $h^{-1}$, from 0.1 $h^{-1}$ to 20 $h^{-1}$, from 1 $h^{-1}$ to 100 $h^{-1}$, from 1 $h^{-1}$ to 75 $h^{-1}$, from 1 $h^{-1}$ to 50 $h^{-1}$, from 1 $h^{-1}$ to 30 $h^{-1}$, from 1 $h^{-1}$ to 20 $h^{-1}$, from 5 $h^{-1}$ to 100 $h^{-1}$, from 5 $h^{-1}$ to 75 $h^{-1}$, from 5 $h^{-1}$ to 50 $h^{-1}$, from 5 $h^{-1}$ to 30 $h^{-1}$, from 5 $h^{-1}$ to 20 $h^{-1}$, from 6 $h^{-1}$ to 100 $h^{-1}$, from 6 $h^{-1}$ to 75 $h^{-1}$, from 6 $h^{-1}$ to 50 $h^{-1}$, from 6 $h^{-1}$ to 30 $h^{-1}$, from 6 $h^{-1}$ to 20 $h^{-1}$, from 10 $h^{-1}$ to 100 $h^{-1}$, from 10 $h^{-1}$ to 75 $h^{-1}$, from 10 $h^{-1}$ to 50 $h^{-1}$, from 10 $h^{-1}$ to 30 $h^{-1}$, from 10 $h^{-1}$ to 20 $h^{-1}$, from 15 $h^{-1}$ to 100 $h^{-1}$, from 15 $h^{-1}$ to 75 $h^{-1}$, from 15 $h^{-1}$ to 50 $h^{-1}$, from 15 $h^{-1}$ to 30 $h^{-1}$, or from 15 $h^{-1}$ to 20 $h^{-1}$.

In embodiments, the feed (light liquid fraction or heavy liquid fraction) may be injected into the first and second steam enhanced catalytic crackers at a gas hourly space velocity of greater than or equal to 0.1 per hour ($h^{-1}$) or greater than or equal to 0.25 $h^{-1}$. The feed may be injected into the steam enhanced catalytic crackers at a gas hourly space velocity of less than or equal to 50 $h^{-1}$, less than or equal to 25 $h^{-1}$, less than or equal to 20 $h^{-1}$, less than or equal to 14 $h^{-1}$, less than or equal to 9 $h^{-1}$, or less than or equal to 5 $h^{-1}$. The feed may be injected into the steam enhanced catalytic crackers at a gas hourly space velocity of from 0.1 $h^{-1}$ to 50 $h^{-1}$, from 0.1 $h^{-1}$ to 25 $h^{-1}$, from 0.1 $h^{-1}$ to 20 $h^{-1}$, from 0.1 $h^{-1}$ to 14 $h^{-1}$, from 0.1 $h^{-1}$ to 9 $h^{-1}$, from 0.1 $h^{-1}$ to 5 $h^{-1}$, from 0.1 $h^{-1}$ to 4 $h^{-1}$, from 0.25 $h^{-1}$ to 50 $h^{-1}$, from 0.25 $h^{-1}$ to 25 $h^{-1}$, from 0.25 $h^{-1}$ to 20 $h^{-1}$, from 0.25 $h^{-1}$ to 14 $h^{-1}$, from 0.25 $h^{-1}$ to 9 $h^{-1}$, from 0.25 $h^{-1}$ to 5 $h^{-1}$, from 0.25 $h^{-1}$ to 4 v, from 1 $h^{-1}$ to 50 $h^{-1}$, from 1 $h^{-1}$ to 25 $h^{-1}$, from 1 $h^{-1}$ to 20 $h^{-1}$, from 1 $h^{-1}$ to 14 $h^{-1}$, from 1 $h^{-1}$ to 9 $h^{-1}$, or from 1 $h^{-1}$ to 5 $h^{-1}$.

In embodiments, the hourly space velocity may be different for the first steam enhanced catalytic cracker as compared to the second steam enhanced catalytic cracker. In one non-limiting example, the light liquid fraction may require lesser hourly space velocities to give more time for the light liquid fraction to be cracked into the desired products. In another non-limiting example, the heavy liquid fraction may require greater hourly space velocities to prevent overcracking of the heavy liquid fraction and prevent excess formation of petroleum coke. In embodiments, the hourly space velocity for the first steam enhanced catalytic cracker may be from 0.1 $h^{-1}$ to 1 $h^{-1}$. In embodiments, the hourly space velocity for the second steam enhanced catalytic cracker may be from 9 $h^{-1}$ to 40 $h^{-1}$.

In embodiments, the first and second steam enhanced catalytic crackers may operate at a temperature of from greater than or equal to 525° C., greater than or equal to 550° C., or greater than or equal to 575° C. The steam enhanced catalytic crackers 114 may be operated at a temperature of less than or equal to 750° C., less than or equal to 675° C., less than or equal to 650° C., or even less than or equal to 625° C. The steam enhanced catalytic crackers 114 may operate at temperatures of from 650° C. to 750° C. or from 675° C. to 750° C. The steam enhanced catalytic crackers 114 may be operated at temperatures of from 525° C. to 750° C., from 525° C. to 675° C., from 525° C. to 650° C., from 525° C. to 625° C., from 550° C. to 675° C., from 550° C. to 650° C., from 550° C. to 625° C., from 575° C. to 675° C., from 575° C. to 650° C., or from 575° C. to 625° C. In other embodiments, the SECC temperature may be from 600 to 750° C. For example, the SECC temperature may be from 600 to 700° C. or from 620 to 680° C. The steam enhanced catalytic crackers 114 may be operated at a pressure of from 0.1 MPa to 0.2 MPa.

As previously discussed, the steam enhanced catalytic crackers 114 may produce olefins, and in particular, light olefins, such as ethylene, propylene, and butylene. In embodiments, the steam enhanced catalytic crackers may additionally produce gasoline as olefins. In embodiments, the ratio of olefins (gasoline) to light olefins produced may change depending on the operating temperatures used in the steam enhanced catalytic crackers 114. For example, operating temperatures between 500° C. to 650° C. may produce primarily propylene and gasoline over ethylene. As operating temperatures increase, the ratio moves further to producing primarily ethylene over propylene and gasoline. For example, operating temperatures between 650° C. to 680° C. may produce equal parts ethylene and propylene with less gasoline. At operating temperatures over 680° C., for example from 680° C. to 750° C., the reaction moves to primarily ethylene.

In embodiments, temperatures at the higher ends (>650° C.) of the operating range may be used to preferentially produce light olefins over heavier olefins, such as ethylene and propylene over gasoline. This may thereby make gasoline a by-product of the steam enhanced catalytic cracking reaction versus a primary product. Further temperature increases (>680° C.) may then minimize the amount of gasoline produced, primarily producing ethylene with propylene as a by-product. It is contemplated that the shifts discussed above may be related to reactions in the steam enhanced catalytic crackers moving from primarily catalytic cracking dominated at lower temperatures (500° C. to 650° C.) to primarily thermal cracking dominated at higher ends of the operating temperatures (>680° C.).

The steam cracking product 121, the dehydrogenated stream 126, and the SECC product 140 may be fractionated to form a light olefins stream 170 and a benzene-toluene-xylene (BTX) stream 180. The streams may be fractionated in a product separator 165. The light olefins stream 170 may comprise light olefins, such as ethylene, propene, and butene. The light olefins stream 170 may comprise at least 70 wt. %, at least 80 wt. %, at least 90 wt. %, at least 95 wt. %, at least 99 wt. %, or at least 99.9 wt. % light olefins, such as ethylene, propene, and butene. The BTX stream 180 may comprise aromatic compounds, such as benzene, toluene, and xylene. For example, the BTX stream 180 may comprise at least 70 wt. %, at least 80 wt. %, at least 90 wt. %, at least 95 wt. %, at least 99 wt. %, or at least 99.9 wt. % of the aromatic compounds.

EXAMPLES

Arab heavy crude oil and Arab extra light crude oil were processed using a computer model using Aspen HYSYS simulation software, according to the systems/configurations in FIGS. 1 and 2. The reaction conditions used in both systems are described below in Table 1. The compositions for the Arab heavy crude oil and the Arab extra light crude oil feeds are illustrated below in Table 2.

As used herein, "T'x' Boiling Point" refers to the temperature at which approximately x % of the components within the crude oil are boiling. For example, "T5 Boiling Point" refers to the temperature at which approximately 5% of the components within the crude oil are boiling. This measurement may also be used to determine the percentage of the feed that has boiling points below a given temperature. For example, if the T5 and T10 boiling points of the Arab heavy crude oil are 56° C. and 103° C. respectively, then the Arab heavy crude oil may include approximately 5% less than 56° C. boiling point hydrocarbon fractions and approximately 5% 56° C. to 103° C. boiling point hydrocarbon fractions.

TABLE 1

| Operating Conditions | | | | | | | |
|---|---|---|---|---|---|---|---|
| Operating Condition | Solvent Deasphalting Unit | Hydro Treater | Gasification Unit | Methane Cracker | Steam Cracker | Dehydrogenation Unit | Steam Enhanced Catalytic Crackers |
| T (° C.) | 120-160 | 280-450 | 700-1200 | 700-1000 | 800-950 | 575-620 | 600-750 |
| P (bar) | 1-40 | 5-160 | 1-29 | 1 | 1 | 1-5 | 1 |
| Solvent/Feed wt. ratio | 2-10 | N/A | N/A | N/A | N/A | N/A | N/A |
| Steam/Feed wt. ratio | N/A | N/A | N/A | N/A | 0.3-0.8 | N/A | 0.3-1.0 |
| $H_2$/Feed wt. ratio | N/A | 0.2-1 | N/A | N/A | N/A | N/A | N/A |
| Catalyst | N/A | NiMo | N/A | Ni/SiO$_2$ | N/A | Pt—Sn/ZrO2 | ZSM-5 |

TABLE 2

| Feed Compositions | | |
|---|---|---|
| Component | Arab Heavy | Arab Extra Light |
| API Gravity [°] | 27.8 | 40.4 |
| Specific Gravity | 0.89 | 0.82 |
| Density [kg/m³] | 887.4 | 822.3 |
| T0 Boiling Point [° C.] | −9 | −12 |
| T5 Boiling Point [° C.] | 56 | 32 |
| T10 Boiling Point [° C.] | 103 | 70 |
| T30 Boiling Point [° C.] | 239 | 161 |
| T50 Boiling Point [° C.] | 358 | 254 |
| T70 Boiling Point [° C.] | 515 | 363 |
| T90 Boiling Point [° C.] | 713 | 532 |
| T95 Boiling Point [° C.] | 805 | 624 |
| T100 Boiling Point [° C.] | 1126 | 856 |

Example 1

As described above, the system of FIG. 1 was entered into the computer model with Arab heavy crude oil as the feed. The results for the simulation are given below in Table 3. The overall yield is the sum of outputs for each of the below treatment units.

TABLE 3

| Steam Cracker | | Hydrotreater | | Steam Enhanced Catalytic Cracker | | Gasification | | Overall Yield | |
|---|---|---|---|---|---|---|---|---|---|
| Component | wt. % | Component | wt. % | Component | wt. % | Component | wt. % | Component | wt. % |
| $C_1 + H_2$ | 13.81 | $C_1 + H_2$ | 2.1 | $C_1 + H_2$ | 3.4 | SynGas | 30.0 | $H_2$ | 0.8 |
| Ethylene | 80.40 | Liquefied Petroleum Gas | 1.3 | $C_2$-$C_4$ paraffins | 8.6 | Residue | 70.0 | C | 1.7 |
| Propylene | 1.68 | Naphtha (185° C. to 204° C.) | 27.1 | $C_2$-$C_4$ olefins | 38.3 | | | Ethylene | 7.5 |
| Butadiene | 1.90 | Distillate (204° C. to 343° C.) | 31.1 | Naphtha and Gasoline | 27.5 | | | Propene | 22.7 |
| Mixed butenes | 0.00 | Gas Oil | 27.3 | Light Cycle Oil | 6.8 | | | Butenes | 14.7 |
| $C_{5+}$ Hydrocarbons | 1.45 | Heavy Cycle Oil & Atmospheric Residue Oil (>340° C.) | 11.1 | Heavy Cycle Oil | 4.1 | | | BTX | 0.0 |
| Benzene | 0.52 | | | Coke | 11.3 | | | Naphtha | 27.6 |
| Toluene | 0.03 | | | | | | | Syngas | 10.3 |
| Fuel Oil | 0.20 | | | | | | | Other | 14.6 |

As is shown in Table 3, the present system results in a yield of nearly 50 wt. % light olefins and no BTX. Although the byproducts naphtha and syngas make up 37 wt. % of the yield, each can be further used in other processes, or further upgraded in recycle streams for the system. For example, the naphtha may be further upgraded to additional light olefins by recycling the naphtha back through the steam cracker. The naphtha may also be further upgraded to BTX if it is processed in, for example, an aromatization unit, including for example, a catalytic reformer and a transalkylation unit. The syngas may also be used to provide energy in the form of heat to the other treatment units. For example, the syngas may be used to heat water for use as steam in the steam cracker or steam enhanced catalytic cracker. The hydrogen within the gasification unit may also be used within the hydroprocessing or hydrocracking unit.

In Table 4, above, "Other" may include crude oil fractions not previously mentioned in the preceding components. Other may also include waste or unusable streams. For example, the Other may include light cycle oils, heavy cycle oils, distillate, and $C_1$, and $C_2$-$C_4$ paraffins. The heavy cycle oil may be used, for example, as fuel oil for boilers.

Example 2

As described above, the system of FIG. 2 was entered into the computer model with Arab extra light crude oil as the feed. The results for the simulation are given below in Table 4. The overall yield is the sum of outputs for each of the below treatment units.

TABLE 4

| Feed Separator | | Steam Cracker | | Hydrotreater | |
|---|---|---|---|---|---|
| Component | wt % | Component | wt % | Component | wt % |
| Percentage C1-C4 hydrocarbon fractions | 2.4 | $C_1 + H_2$ | 17.49 | $C_1 + H_2$ | 1.3 |
| Percentage <300° C. boiling point hydrocarbon fractions | 52.7 | Ethylene | 62.69 | Liquefied Petroleum Gas | 0.0 |
| Percentage >300° C. boiling point hydrocarbon fractions | 44.9 | Propylene | 7.83 | Naphtha (185° C. to 204° C.) | 5.9 |
| | | Butadiene | 2.55 | Distillate (204° C. to 343° C.) | 28.3 |
| | | Mixed butenes | 0.00 | Gas Oil | 46.8 |
| | | $C_{5+}$ | 6.71 | Heavy Cycle Oil & Atmospheric Residue Oil (>340° C.) | 17.7 |
| | | Benzene | 1.71 | | |
| | | Toluene | 0.39 | | |
| | | Fuel Oil | 0.63 | | |

| SECC for Light Liquid Fraction | | SECC for Heavy Liquid Fraction | | Gasification | | Overall Yields | |
|---|---|---|---|---|---|---|---|
| Component | wt % | Component | wt % | Component | wt % | Component | wt % |
| $C_1 + H_2$ | 9.9 | $C_1 + H_2$ | 2.9 | Syngas | 30.0 | $H_2$ | 2.6 |
| $C_2$-$C_4$ paraffins | 5.3 | $C_2$-$C_4$ paraffins | 8.8 | Residue | 70.0 | Coke | 1.9 |

TABLE 4-continued

| | | | | | |
|---|---|---|---|---|---|
| $C_2$-$C_4$ olefins | 57.2 | $C_2$-$C_4$ olefins | 39.9 | Ethylene | 22.9 |
| Naphtha and Gasoline | 17.2 | Naphtha and Gasoline | 16.6 | Propene | 25.0 |
| Light Cycle Oil | 7.7 | Light Cycle Oil | 11.8 | Butenes | 13.6 |
| Heavy Cycle Oil | 0.4 | Heavy Cycle Oil | 15.5 | BTX | 0.2 |
| Coke | 2.3 | Coke | 4.5 | Naphtha | 18.7 |
| | | | | Other | 15.1 |

As is shown in Table 4, the present system results in a yield of 61.5 wt. % light olefins and almost BTX. Although the byproducts naphtha and syngas make up nearly 34 wt. % of the yield, each of the previous can be further used in other processes, or further upgraded in recycle streams for the system, as previously discussed. The naphtha especially may be further upgraded for example in a aromatization unit to upgrade the naphtha into BTX.

It is also noted that recitations herein of "at least one" component, element, etc., should not be used to create an inference that the alternative use of the articles "a" or "an" should be limited to a single component, element, etc.

Having described the subject matter of the present disclosure in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Further, it will be apparent that modifications and variations are possible without departing from the scope of the present disclosure, including, but not limited to, embodiments defined in the appended claims. More specifically, although some aspects of the present disclosure are identified herein as preferred or particularly advantageous, it is contemplated that the present disclosure is not necessarily limited to these aspects.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

What is claimed is:

1. A process for the conversion of a petroleum feed to light olefins, the process comprising:
   pretreating the petroleum feed to form one or more pretreated petroleum feeds;
   fractionating the one or more pretreated petroleum feeds to form a methane stream, an ethane stream, a $C_3$-$C_4$ stream, a light liquid fraction and a heavy liquid fraction;
   methane cracking the methane stream to form hydrogen;
   steam cracking the ethane stream to form a steam cracking product;
   dehydrogenating the $C_3$-$C_4$ stream to form a dehydrogenated stream;
   steam enhanced catalytic cracking (SECC) the light liquid fraction in a first steam enhanced catalytic cracker to form a light liquid SECC product; and
   steam enhanced catalytic cracking the heavy liquid fraction in a second steam enhanced catalytic cracker to form a heavy liquid SECC product, and wherein
   a first steam to feed ratio of the first steam enhanced catalytic cracker is less than a second steam to feed ratio of the second steam enhanced catalytic cracker, the first steam to feed ratio is from 0.2 to 0.8, and the second steam to feed ratio is from 0.8 to 1.0.

2. The process of claim 1, wherein pretreating the petroleum feed comprises solvent deasphalting the petroleum feed.

3. The process of claim 2, wherein the solvent deasphalting the petroleum feed comprises contacting the petroleum feed with a solvent at a temperature of 120-160° C., a pressure of 2-6 MPa, and a solvent/feed ratio of 3-6.

4. The process of claim 1, wherein pretreating the petroleum feed comprises gasification of an asphaltene stream.

5. The process of claim 4, wherein gasification of the asphaltene stream comprises exposing the asphaltene stream to a temperature of from 700 to 1200° C. and a pressure of from 1 to 29 bar.

6. The process of claim 1, wherein pretreating the petroleum feed comprises hydroprocessing a deasphalted oil stream.

7. The process of claim 6, wherein the hydroprocessing is hydrotreating and hydrotreating the deasphalted oil stream comprises contacting the deasphalted oil stream with a hydrogen stream at a temperature of from 280 to 450° C. and a pressure of from 5 to 160 bar.

8. The process of claim 1, further comprising fractionating the steam cracking product, the dehydrogenated stream, and the SECC product to form a light olefins stream and a benzene-toluene-xylene (BTX) stream.

9. The process of claim 1, further comprising:
   methane cracking a methane recycle stream;
   steam cracking a steam cracking recycle stream; and
   dehydrogenating a dehydrogenation recycle stream.

10. The process of claim 1, wherein the petroleum feed is a whole crude.

11. The process of claim 1, wherein:
    the light liquid fraction comprises $C_5$ hydrocarbons to a 300° C. cut point; and
    the heavy liquid fraction comprises hydrocarbons with at least a 300° C. cut point.

12. The process of claim 11 wherein the whole crude is an Arab Extra Light, Arab Light, or Arab Heavy.

13. The process of claim 1, wherein SECC comprises contacting hydrocarbons with a catalyst at a reaction temperature of 600 to 750° C.

14. The process of claim 1, wherein SECC comprises contacting hydrocarbons with a ZSM-5 based catalyst.

15. The process of claim 1, wherein dehydrogenating the $C_3$-$C_4$ stream comprises contacting the $C_3$-$C_4$ stream with a dehydrogenation catalyst at a temperature of from 575° C. to 620° C. and a pressure of from 2 to 5 bar.

16. The process of claim 1, further comprising fractionating the petroleum feed to produce a light crude fraction and steam enhanced catalytic cracking the light crude fraction.

* * * * *